(12) United States Patent
Keller

(10) Patent No.: US 7,569,067 B2
(45) Date of Patent: Aug. 4, 2009

(54) INSERTION INSTRUMENT FOR CERVICAL PROSTHESES

(75) Inventor: Arnold Keller, Kayhude (DE)

(73) Assignee: Cervitech, Inc., Rockaway, NJ (US)

( * ) Notice: Subject to any disclaimer, the term of this patent is extended or adjusted under 35 U.S.C. 154(b) by 571 days.

(21) Appl. No.: 11/155,597

(22) Filed: Jun. 20, 2005

(65) Prior Publication Data
US 2006/0004377 A1   Jan. 5, 2006

Related U.S. Application Data

(63) Continuation of application No. 10/619,180, filed on Jul. 15, 2003, now abandoned.

(51) Int. Cl.
*A61B 17/00* (2006.01)
(52) U.S. Cl. ...................... 606/206; 606/208
(58) Field of Classification Search .............. 606/89, 606/90, 99, 105, 205, 208; 623/17.16
See application file for complete search history.

(56) References Cited

U.S. PATENT DOCUMENTS

| | | |
|---|---|---|
| 3,960,147 A | 6/1976 | Murray |
| 4,759,766 A | 7/1988 | Buettner-Janz et al. |
| 4,997,432 A | 3/1991 | Keller |
| 5,122,130 A * | 6/1992 | Keller ............... 606/86 A |
| 5,314,477 A | 5/1994 | Marnay |
| 5,431,658 A | 7/1995 | Moskovich |
| 5,556,431 A | 9/1996 | Büttner-Janz |
| 5,720,751 A | 2/1998 | Jackson |
| 6,368,350 B1 | 4/2002 | Erickson et al. |
| 6,402,785 B1 | 6/2002 | Zdeblick et al. |
| 6,478,800 B1 | 11/2002 | Fraser et al. |
| 6,517,580 B1 | 2/2003 | Ramadan et al. |
| 6,755,841 B2 | 6/2004 | Fraser et al. |
| 6,981,990 B2 | 1/2006 | Keller |
| 7,118,580 B1 | 10/2006 | Beyersdorff et al. |
| 2002/0072752 A1 * | 6/2002 | Zucherman et al. ........ 606/99 |
| 2003/0069586 A1 | 4/2003 | Errico et al. |
| 2003/0083747 A1 | 5/2003 | Winterbottom et al. |

FOREIGN PATENT DOCUMENTS

| | | |
|---|---|---|
| EP | 1 306 064 A1 | 5/2003 |
| WO | WO 01/19295 A1 | 3/2001 |

* cited by examiner

*Primary Examiner*—Todd E Manahan
*Assistant Examiner*—Michael G Mendoza
(74) *Attorney, Agent, or Firm*—Morrison & Foerster LLP

(57) ABSTRACT

An insertion instrument for a multi-part intervertebral endoprosthesis includes two closure plates and a sliding core arranged between these, said insertion instrument having a handgrip part, gripping members which hold the closure plates between them, and a force-receiving part for applying an insertion force to the intervertebral endoprosthesis, the gripping members being guided movably toward and away from one another via a hinge and being able to be tensioned against the intervertebral endoprosthesis, projections pointing in the tensioning direction or recesses for holding the intevertebral endoprosthesis with form-fit being provided on the gripping members, and a block guided in the longitudinal axis direction and with an abutment surface being provided which can be moved by means of an actuating device so as to bear on the intervertebral endoprosthesis and, in its forward position, secures the intevertebral endoprosthesis against the projections or recesses.

10 Claims, 2 Drawing Sheets

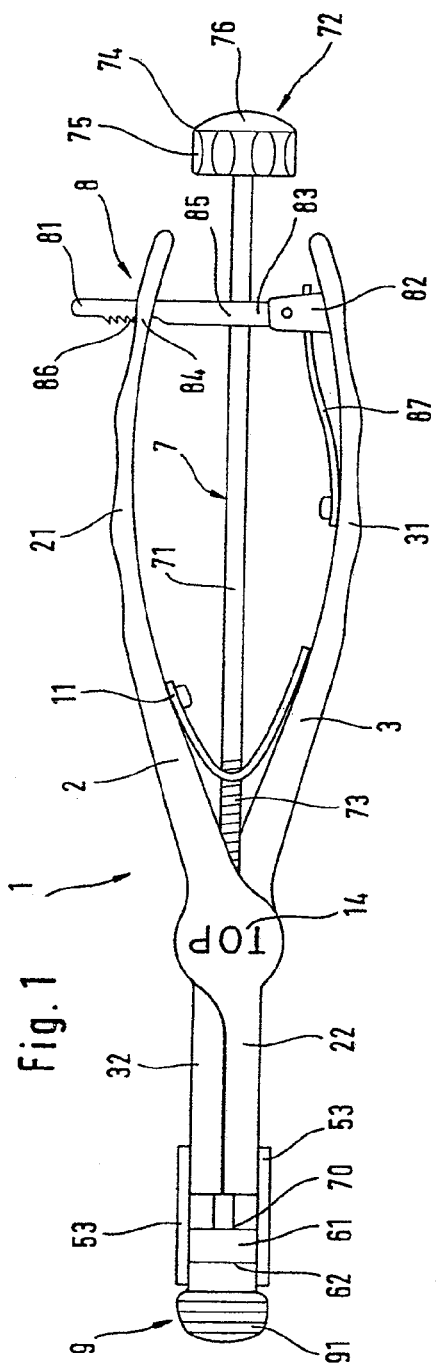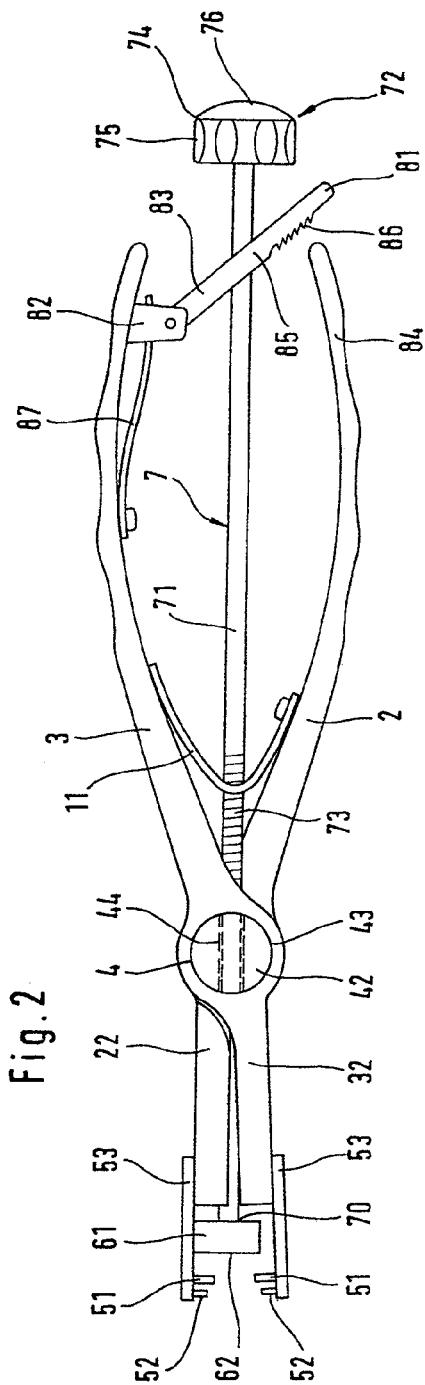

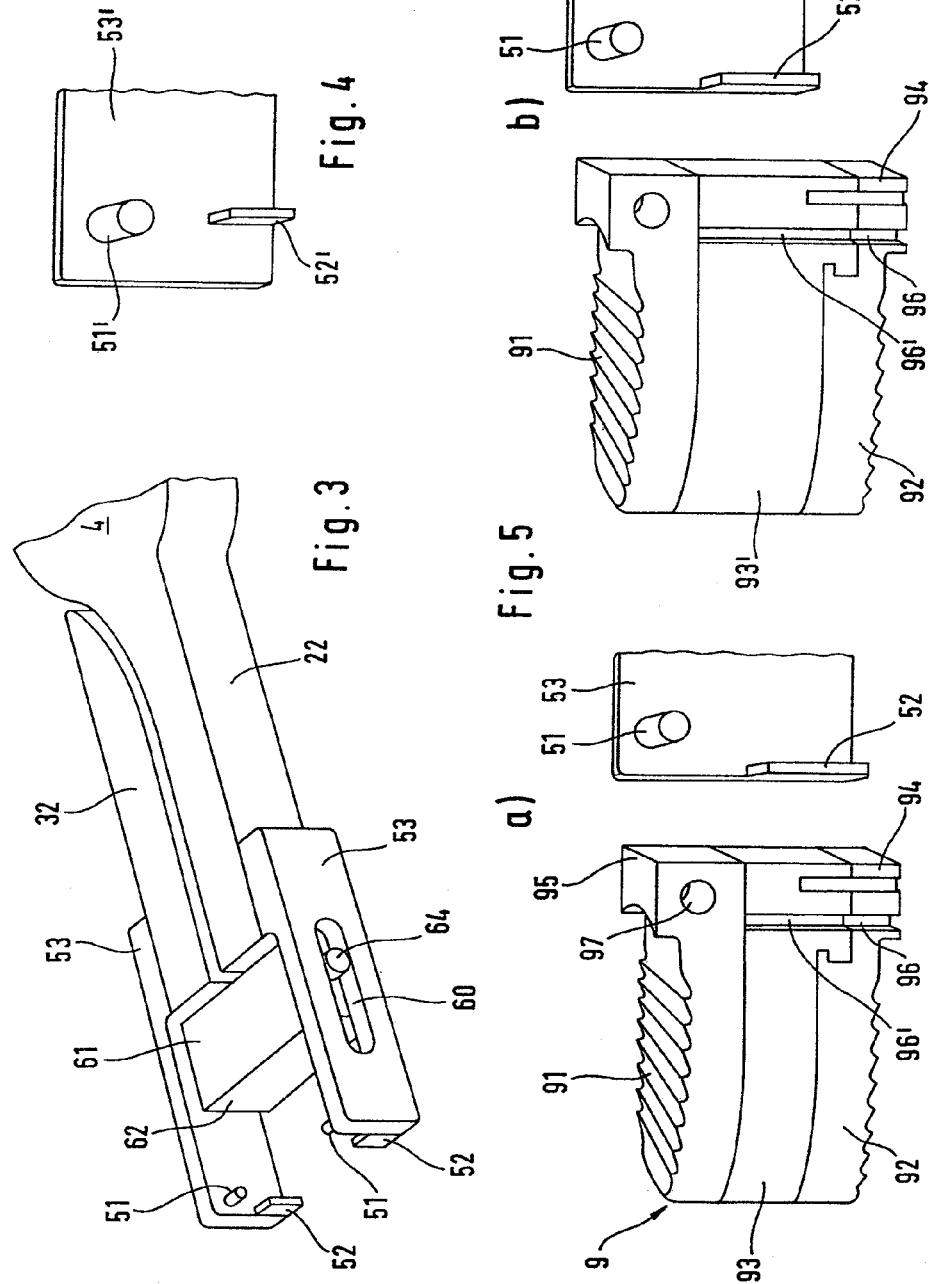

INSERTION INSTRUMENT FOR CERVICAL PROSTHESES

REFERENCE TO RELATED APPLICATION

This application is a continuation of Ser. No. 10/619,180, filed Jul. 15, 2003, now abandoned.

FIELD AND BACKGROUND OF THE INVENTION

The invention relates to an insertion instrument for a multi-part intervertebral endoprosthesis which comprises two closure plates and a sliding core arranged between these, said insertion instrument having a handgrip part, gripping members which hold the closure plates between them, and a force-receiving part for applying an insertion force to the intervertebral endoprosthesis.

For inserting intervertebral prostheses, an insertion instrument is known (EP-A-1 306 064) which, at its front end, has two prosthesis holders for receiving in each case a prosthesis plate and which consist of two gripping members which are connected rigidly to one another and which hold the plates between them by friction. For very small implants, of the kind which are used in the area of the cervical spine and which have to be positioned very precisely, this may be too unreliable.

SUMMARY OF THE INVENTION

The object of the invention is to make available an improved instrument for implantation of intervertebral prostheses which is adapted in particular to the requirements of implantation in confined conditions, as apply in particular in the area of the cervical spine.

The solution according to the invention lies in an insertion instrument for a multi-part intervertebral endoprosthesis that includes two closure plates and a sliding core arranged between the closure plates, an insertion instrument that includes a handgrip part, gripping members which hold the closure plates between them, a hinge, a force-receiving part for applying an insertion force to the intervertebral endoprosthesis, either projections pointing in a tensioning direction or recesses for holding the intervertebral endoprosthesis with a form-fit that are formed on the gripping members, and a block guided in the longitudinal axis direction and provided with an abutment surface configured to be movable by an actuating device so as to bear on the intervertebral endoprosthesis and, in a forward position, so as to secure the intervertebral endoprosthesis against the projections or recesses. The gripping members are configured to be guided movably toward and away from one another via the hinge and to be tensioned against the intervertebral endoprosthesis. The preferred embodiments set forth other advantageous features of the invention.

In the case of an insertion instrument for a multi-part intervertebral endoprosthesis, in particular a cervical prosthesis, which comprises two closure plates and a sliding core arranged between these, said insertion instrument having a handgrip part, gripping members which hold the closure plates between them, and a force-receiving part for applying an insertion force to the intervertebral endoprosthesis, the invention provides that the gripping members are guided movably toward and away from one another via a hinge and are able to be tensioned against the intervertebral endoprosthesis, projections pointing in the tensioning direction or recesses for holding the intervertebral endoprosthesis with a form-fit are formed on the gripping members, and a block guided in the longitudinal axis direction and with an abutment surface is provided which can be moved to the intervertebral endoprosthesis by means of an actuating device and, in its forward position, secures the intervertebral endoprosthesis against the projections or recesses. When the forceps-like insertion instrument is closed, the gripping members connected to one another via a hinge move toward one another and engage with a form-fit via their projections (or recesses) in corresponding depressions (or elevations) of the intervertebral endoprosthesis and thus tension the latter in a direction transverse to the longitudinal axis of the insertion instrument. The longitudinally movably guided block can be moved toward the intervertebral endoprosthesis until its abutment surface bears on the intervertebral endoprosthesis and secures the latter against the projections (or recesses). In this way, the intervertebral endoprosthesis is also tensioned in the longitudinal direction. It is thus held by the insertion instrument in a manner free of play and in a precise position. By virtue of the block bearing firmly on the intervertebral endoprosthesis, considerable forces, such as arise when striking the intervertebral endoprosthesis into place, can also be safely transmitted. Since these considerable forces are transmitted via the block and its abutment surface, the projections (or recesses) do not have to take up these forces. They can be of fairly small dimension and therefore made very fine, as is desired for precise positioning, without having to take into consideration the high force transmission when striking the intervertebral endoprosthesis home. In addition, by bearing on the intervertebral endoprosthesis, the block ensures that the latter does not inadvertently turn and that its individual elements do not open. By virtue of the invention, the intervertebral endoprosthesis can thus be held easily, safely and with precise positioning on the insertion instrument and inserted.

A number of terms are explained below:

The longitudinal axis of the forceps is understood as the center line which is the angle bisector between the handgrip parts of the forceps halves and the jaw parts of the forceps halves.

The tensioning direction is understood as the direction in which the gripping members move toward one another. The opposite direction is the spreading direction. These directions are generally approximately transverse to the longitudinal axis of the insertion instrument.

A form-fit hold is understood as meaning that the projections engage in correspondingly shaped receiving openings of the intervertebral endoprosthesis, or vice versa. Viewed in the direction of the longitudinal axis, the projections grip into an undercut.

The insertion instrument is preferably designed as a forceps, whose jaw parts form the gripping members. This permits a space-saving construction and easy handling, which is of advantage particularly in the confined conditions in the area of the cervical spine.

To make it simpler to use, the actuating device has a rod with a handle arranged in the rear area of the handgrip part. This allows the operating surgeon to use the actuating device without awkward maneuvering. Because of the small space available in the case of cervical prostheses, this is of particular importance when removing the insertion instrument after introduction of the intervertebral endoprosthesis, when the block has to be moved back. For this purpose, the rod is expediently provided with a screw thread and is guided in a counterthread which is fixed on the instrument and arranged preferably in the hinge. Thus, by turning in one direction, the block can be guided toward the intervertebral endoprosthesis and thus secure it, whereas, by turning in the opposite direction, the block is moved away and releases the intervertebral endoprosthesis for the purpose of removal of the insertion instrument. The screw device also has the advantage of being self-locking, with the result that a separate securing device for protection against inadvertent displacement is not necessary. However, a screw device is not absolutely necessary, and, instead, other preferably self-locking actuating devices can also be provided.

In a particularly advantageous construction, the actuating device is guided through the hinge. This is not only a particularly space-saving design, it also guarantees a near-center arrangement. This arrangement ensures that the insertion instrument does not deviate to the side even under high forces when struck. A high degree of positioning precision when inserting the intervertebral endoprosthesis is achieved in this way.

It is expedient for the actuating device to have a strike head at its handgrip end. In this way, via the actuating device and the block, it is possible to act directly on the intervertebral endoprosthesis so as to bring it to its implantation site. For this purpose, it is expedient for the handle itself to be designed as a strike head. This permits a space-saving construction, which is of considerable value particularly in the confined conditions in the area of the cervical spine.

In order to ensure that the insertion instrument does not inadvertently spring open, even when acted upon by considerable force, a locking device is expediently provided for securing the handgrip parts in the position when pressed together, said locking device having a guide for the actuating device. This ensures that the actuating device does not deflect outward under high loads, particularly when the strike head is arranged far to the rear. The locking device can be provided at the rear end of the handgrip parts in a manner known per se. It is important that it is sufficiently strongly dimensioned to withstand the loads which occur during striking but can nevertheless be easily released for removing the instrument.

In an expedient embodiment, the projections or recesses are arranged on jaw inserts which are fastened releasably on the jaw parts. This means that, if necessary, it is easy to exchange the jaw inserts together with the projections or recesses arranged thereon, in order to adapt the insertion instrument to other types or sizes of intervertebral endoprostheses.

BRIEF DESCRIPTION OF THE DRAWINGS

The invention is explained below with reference to the drawing in which an advantageous illustrative embodiment is shown, and where:

FIG. 1 shows an overall view of the insertion instrument according to the invention, seen from above, with an intervertebral endoprosthesis;

FIG. 2 shows an overall view of the insertion instrument according to the invention seen from below;

FIG. 3 shows an enlarged detail view of a jaw part of the insertion instrument, in a longitudinal axis section;

FIG. 4 shows a detail view of the other jaw insert; and

FIG. 5 shows a detail view of the insertion instrument with an intervertebral endoprosthesis arranged thereon.

DETAILED DESCRIPTION OF THE INVENTION

The illustrative embodiment, shown in the figures, of an insertion instrument according to the invention is a forceps, labeled as a whole by reference number 1. It is used for inserting cervical prostheses 9 into the intervertebral space of two adjacent vertebral bodies of the cervical spine (not shown).

The forceps 1 is made up of two forceps halves 2, 3 which are connected to one another movably via a pivot hinge 4. In their rear area, the forceps halves 2, 3 have a respective handgrip part 21, 31 and in their front area they have a respective jaw part 22, 32. The pivot hinge 4 is arranged at the transition between the handgrip parts 21, 31 and the jaw parts 22, 32. It is formed by a pin 42 on the forceps half 2 (in FIG. 1 it extends upward from the plane of the drawing), which pin 42 is mounted in a matching opening 43 in the central area of the other forceps half 3. The bearing pin 42 has a through-bore 44 which runs from the handgrip area of the forceps halves 2, 3 to the jaw area. It will be discussed in more detail later. The pivot hinge 4 allows the handgrip parts 21, 31 of the forceps halves 2, 3 to be moved toward one another so that the jaw parts 22, 32 close, and vice versa.

The jaw parts 22, 32 function as gripping members. In the front area, on their mutually facing inner surfaces, they each have two projections 51, 52 pointing in the tensioning direction 12. These projections are not arranged directly on the jaw parts 22, 32, but instead on jaw inserts 53 which are secured exchangeably, by means of a screw (not shown), in a corresponding recess on the outer surfaces of the jaw parts 22, 32. Each jaw insert 53 has a projection 51 and a projection 52. The projection 51 is formed like a pin and is located in the upper area of the jaw insert 53, while the projection 52 is formed like a small plate and is located in the lower area of the jaw insert 53. The dimensions and arrangement of the projections 51, 52 are adapted to corresponding receiving openings on the cervical prostheses 9 to be received. This will be explained in more detail later.

Arranged on the jaw part 22 there is a guide rail 60 which holds a block 61 such that the latter is longitudinally displaceable in the forward and rearward directions on the forceps half 2. The guide rail 60 is designed as an elongate hole in the jaw insert 53 of the jaw part 32. A grub screw arranged laterally in the block 61 engages in the oblong hole forming the guide rail 60 and guides the block in the longitudinal direction. Instead of the oblong hole, other guide elements can also be provided which allow the block 61 to be guided in forward and rearward movement in the longitudinal direction, for example a dovetail guide. At its front end, the block 61 is provided with an abutment surface 62 designed to cooperate with the cervical prosthesis 9.

The block 61 is engaged by an actuating device 7 which extends from the rear area of the block 61 via the through-bore 44 and into the area between the handgrip parts 21, 31. The actuating device 7 comprises a coupling element 70 for connection to the block 61, which, in the illustrative embodiment shown, is a vertebra support suitable for transmitting shear forces, and it moreover comprises a rod 71 and a handle 72 for actuation. Provided in the front area of the rod 71 there is an external thread 73 which cooperates with a complementary internal thread (not shown) in the through-bore 44 of the pin 42 as an instrument-fixed guide. By turning the handle 72, it is thus possible for the rod 71, and with it the block 61 via the coupling element 70, to be moved backward and forward along the guide rail 60. The handle 72 is designed as a rotatable knob which, on its outer circumference 74, has a suitable surface finish, for example a coarse ribbing 75, to allow the operating surgeon a good grip.

The rear end of the handle 72 is provided with a convex bulge 76. It serves as a strike head for the actuating device 7. Impulses acting on the bulge 76 of the strike head are transmitted by this via the rod 71 of the actuating device 7, the shear-resistant vertebral support 70 and the block 61, to the latter's abutment surface 62.

A locking device 8 for the handgrip parts 21, 31 is provided in the rear area of the forceps 1. This locking device 8 comprises a pivotably movable catch element 83 and a locking pawl 84 (which are arranged opposite one another on the handgrip parts 21, 31), a release device 81, a base 82 and a spring 87. The rear end of the handgrip part 21 is designed as a fork, the locking pawl 84 being formed by a beveling of the base of the fork. The catch element 83 is mounted by the base 82 in the plane enclosed by the handgrip parts 21, 31. The spring 87 is designed as a leaf spring and acts on that end of the catch element 83 mounted in the base 82 in such a way that it is pressed forward to the locking pawl 84. Starting from the base 82, the catch element 83 has a wide area and a narrow area. In its narrow area, the catch element 83 has, on its front face, a toothing 86 into which, when the forceps 1 is closed, the locking pawl 84 engages and is locked, so that the handgrip parts 21, 31 cannot move away from one another and, as a result, the insertion instrument 1 is safeguarded against inadvertently springing open. In this way, it is possible for even substantial loads, for example hammer strikes, to be applied to the bulge 76 on the forceps 1 without any fear of inadvertent opening and without the operating surgeon needing to secure the handgrip parts 21, 31 by manual force against undesired opening. To open the forceps 1 after implantation has been carried out, the catch element 83 is pivoted rearward by applying rearward pressure on the release element 81, by which means the locking pawl 84 is freed from the catch element 83, and the handgrip parts 21, 31 thus move apart from one another under the action of the spring 11. With the forceps 1 in the opened state, the catch element 83 is pivoted rearward counter to the force of the spring 87. Provided in the wide area of the catch element 83 there is a guide 85 which is designed as an oblong hole and which is used to hold the rod 71, even when the forceps 1 is open, in a defined position in the longitudinal axis 10 and to avoid deflection of the rod 71 even under high loads.

Also fixed on the handgrip part 31 there is a leaf spring 11 which is guided round the rod 71 to the other handgrip part 21. With the forceps 1 closed, this leaf spring 11 is tensioned and has the effect that, after release of the catch elements 82 83, the insertion instrument 1 automatically opens to permit removal.

The cooperation with the cervical prosthesis 9 will be described now with reference to FIGS. 3 and 5. The cervical prosthesis 9 consists of an upper closure plate 91 and a lower closure plate 92, with a pivot [sic] element 93 arranged between them. The cervical prosthesis 9 is intended for implantation in the interspace between two adjacent vertebrae of a human cervical spine. The top closure plate 91 is secured to the upper vertebra and the bottom closure pate 92 is secured to the lower vertebra. To arrange the cervical prosthesis 9 securely on the forceps 1 for insertion into the intervertebral space, the top and bottom closure plates 91, 92 have receiving openings on their lateral flanks in the area of their front flange 94, 95. The receiving opening on the top closure plate 91 is designed as a bore 97 with an additional countersink. The receiving opening on the bottom closure plate 92 is designed as a slit 96. In its flange-side area, the sliding core 93 is likewise provided with a slit 96' which is arranged in such a way that it is flush with the slit 96 of the bottom closure plate 92. The slits 96, 96' thus result in a continuous groove.

To receive the cervical prosthesis 9 with the forceps 1, the cervical prosthesis 9 is brought into the area between the jaw parts 22, 32 and the forceps 1 is closed, as a result of which the jaw parts 22, 32 move toward one another. In so doing, the projections 51, 52 engage in the corresponding receiving openings of the two closure plates 91, 92, the pins 51 engaging in the bore 97 and the small plates 52 engaging in the slits 96, 96'. In this way, the cervical prosthesis 9, in the tensioning direction, is held free from play on the forceps 1. The different design of the projections 51, 52 and of the receiving openings configured as bores 97 and slits 96 ensures that the cervical prosthesis 9 can be held on the forceps 1 only with the correct orientation. If, as in the illustrated embodiment, the forceps 1 is additionally provided with a marking 14 for the top, this virtually eliminates the possibility of incorrect implantation as a result of incorrect orientation of the cervical prosthesis 9. After the cervical prosthesis 9 has in this way been received in the correct orientation on the forceps 1, the rod 71 can be moved forward via the actuating device 7 by turning the handle 72, with the result that the block 61 comes to lie, from the rear, with its abutment surface 62 on the flange 94, 95 of the cervical prosthesis 9. In doing so, the block 61 tensions the cervical prosthesis 9 against the projections 51, 52 and thus orients the cervical prosthesis 9 in a defined position. Any play existing in the longitudinal axis direction between the projections 51, 52 and the bores 97 and the slits 96 is compensated in this way. The cervical prosthesis 9 is thus held securely and in a precise position on the forceps 1. In addition, the fact that the block 61 bears on the flanges 93, 94 of the two closure plates 91, 92 ensures that the two closure plates 91, 92 do not move away from one another at their front end. This eliminates the possibility of the cervical prosthesis 9 opening, which would prevent successful introduction into the intervertebral space.

It is furthermore made possible to implant cervical prostheses of different height without making changes to the forceps 1. FIG. 3b shows a cervical prosthesis 9' which has a thicker sliding core 93'. Like the sliding core 93, it is provided with a slit 96" which is flush with the slit 96 of the bottom closure plate 92. This configuration of the receiving opening on the bottom closure plate 92 as a slit 96 and its continuation as slit 96" in the sliding core 93' ensure that the thicker cervical prosthesis 9' can be gripped and securely held with the same forceps 1 without changing the arrangement of the projections 51, 52. The positioning precision is in this case guaranteed by the pin-like projections 51 which engage in the bores 97.

If necessary, however, it is also possible to provide other jaw inserts 53' which have a different arrangement of the projections 51', 52', as is shown in FIG. 4. In this way, the forceps 1 can be adapted to other intervertebral endoprostheses, for example to particularly small ones for treatment of children.

With its abutment surface 62, the block 61 affords a sufficiently large force transmission surface for transmitting to the cervical prosthesis 9 the impulses applied to the bulge 76 acting as the strike head. The great advantage of this is that the projections 51, 52, which have been finely dimensioned in the interest of precise positioning, do not have to transmit the strike forces, so that the risk of bending or even breaking of the projections 51, 52 as a result of overloading is excluded, by virtue of the block 61 and its abutment surface 62 assuming the role of force transmission.

The forceps 1 according to the invention allows the cervical prosthesis 9 to be arranged with precise positioning and without any risk of its being the wrong way round on the forceps 1, thereby preventing any undesired opening of the cervical prosthesis 9. Moreover, by virtue of the block 61 with the abutment surface 62, it also permits transmission of forces even in the case of forceps 1 of small dimensions. In this way, reliable implantation of the prosthesis is guaranteed. The small dimensions of the forceps 1 also has the advantage that it gives the operating surgeon good access to and a good overall view of the implantation site.

The invention claimed is:

1. A multi-part intervertebral endoprosthesis system, comprising:
    an intervertebral endoprosthesis comprising two closure plates and a sliding core arranged between the closure plates; and
    an insertion instrument configured for inserting the intervertebral endoprosthesis between adjacent vertebrae, the insertion instrument comprising:
    a handgrip part,
    gripping members configured to clamp the closure plates therebetween in a clamping direction,
    a hinge,
    a force-receiving part for applying an insertion force to the intervertebral endoprosthesis,
    a block guided in the longitudinal axis direction of the insertion instrument, and an actuating device,
    wherein the block is provided with an abutment surface and configured to be movable by the actuating device in a tensioning direction different from the clamping direction;
    the hinge is configured to allow the gripping members to move toward and away from each other in the clamping direction to clamp and to release the intervertebral endoprosthesis:
    either a projection or an interlocking recess is provided on the intervertebral endoprosthesis, and a corresponding interlocking recess or a corresponding projection is provided on at least one of the gripping members, the projection pointing in the clamping direction and being configured to provide a form-fit with the interlocking recess in the tensioning direction; the block is configured so as to bear on the intervertebral endoprosthesis and, in a forward position, so as to secure the intervertebral endoprosthesis in the tensioning direction against the form-fit of the projection and the interlocking recess; the insertion instrument is designed as forceps whose jaw parts from the gripping parts; and the actuating device is guided through the hinge.

2. The multi-part endoprosthesis system according to claim 1, wherein the actuating device is a rod with a handle arranged in the rear area of the handgrip part.

3. The multi-part endoprosthesis system according to claim 2, wherein the rod is provided with a screw thread and is guided in a counter thread which is fixed on the instrument and arranged in the hinge.

4. The multi-part endoprosthesis system according to claim 2, wherein the handle is designed as a strike head.

5. The multi-part endoprosthesis system according to claim 1, further comprising a locking device provided for securing the handgrip parts in the position when pressed together, the locking device having a guide for the actuating device.

6. The multi-part endoprosthesis system according to claim 1, wherein the projection is provided on a jaw insert which is fastened releasably on the at least one of the gripping members, and the recess is provided on the intervertebral endoprosthesis.

7. The multi-part endoprosthesis system according to claim 5, wherein the actuating device is a rod with a handle arranged in the rear area of the handgrip part.

8. The multi-part endoprosthesis system according to claim 6, wherein the actuating device is a rod with a handle arranged in the rear area of the handgrip part.

9. The multi-part endoprosthesis system according to claim 3, further comprising a locking device provided for securing the handgrip parts in the position when pressed together, the locking device having a guide for the actuating device.

10. The multi-part endoprosthesis system according to claim 6, further comprising a locking device provided for securing the handgrip parts in the position when pressed together, the locking device having a guide for the actuating device.

* * * * *

UNITED STATES PATENT AND TRADEMARK OFFICE
CERTIFICATE OF CORRECTION

PATENT NO.         : 7,569,067 B2                                              Page 1 of 1
APPLICATION NO.    : 11/155597
DATED              : August 4, 2009
INVENTOR(S)        : Arnold Keller It is certified that error appears in the above-identified patent and that said Letters Patent is hereby corrected as shown below:

In Claim 1, column 8, line 3, please replace "from" with --form--.

Signed and Sealed this

Twenty-ninth Day of September, 2009

David J. Kappos
*Director of the United States Patent and Trademark Office*